United States Patent
Hillmann et al.

(10) Patent No.: US 9,134,111 B2
(45) Date of Patent: Sep. 15, 2015

(54) METHOD FOR OPTICAL TOMOGRAPHY

(71) Applicants: UNIVERSITAT ZU LUBECK, Lubeck (DE); MEDIZINISCHES LASERZENTRUM LUBECK GMBH, Lubeck (DE); THORLABS GMBH, Dachau (DE)

(72) Inventors: Dierck Hillmann, Lubeck (DE); Gereon Huttmann, Lubeck (DE); Peter Koch, Lubeck (DE); Christian Luhrs, Niendorf (DE); Alfred Vogel, Lubeck (DE)

(73) Assignees: Universitat Zu Lubeck, Lubeck (DE); Medizinisches Laserzentrum Lubeck GmbH, Lubeck (DE); Thorlabs GmbH, Dachau (DE)

( * ) Notice: Subject to any disclaimer, the term of this patent is extended or adjusted under 35 U.S.C. 154(b) by 13 days.

(21) Appl. No.: 14/058,966

(22) Filed: Oct. 21, 2013

(65) Prior Publication Data

US 2014/0092392 A1    Apr. 3, 2014

Related U.S. Application Data

(63) Continuation of application No. PCT/EP2012/001639, filed on Apr. 16, 2012.

(60) Provisional application No. 61/508,831, filed on Jul. 18, 2011.

(30) Foreign Application Priority Data

Apr. 21, 2011   (DE) .................... 10 2011 018 603

(51) Int. Cl.
*G01B 11/02* (2006.01)
*G01B 9/02* (2006.01)
*G01N 21/47* (2006.01)
*G03H 1/00* (2006.01)
*A61B 5/00* (2006.01)
*G03H 1/04* (2006.01)

(52) U.S. Cl.
CPC ........ *G01B 9/02091* (2013.01); *G01B 9/02004* (2013.01); *G01B 9/02029* (2013.01); *G01N 21/4795* (2013.01); *G03H 1/0011* (2013.01); *A61B 5/0066* (2013.01); *G03H 2001/005* (2013.01); *G03H 2001/0038* (2013.01); *G03H 2001/0458* (2013.01); *G03H 2001/0467* (2013.01); *G03H 2210/12* (2013.01); *G03H 2210/62* (2013.01)

(58) Field of Classification Search
CPC ........... G01B 9/02091; G01B 9/02047; G01B 9/02083; G01B 9/02085; G01B 11/2441; G01N 21/4795
USPC .......................................................... 356/497
See application file for complete search history.

(56) References Cited

U.S. PATENT DOCUMENTS

| 6,002,480 A * | 12/1999 | Izatt et al. ..................... 356/479 |
| 2008/0137933 A1 * | 6/2008 | Kim ............................. 382/131 |

OTHER PUBLICATIONS

Potcoava et al., "Otpical tomography for biomedical applications by digital interference holography", May 23, 2008, IOP Publishing, pp. 1-8.*

*Primary Examiner* — Jonathan Hansen
(74) *Attorney, Agent, or Firm* — Graham Curtin, P.A.

(57) ABSTRACT

There is disclosed a method for detecting spatially structured sample volumes by means of coherent light and digital holography. There is also disclosed a method for analyzing the depth structure of samples in accordance with optical coherence tomography.

9 Claims, 3 Drawing Sheets

METHOD FOR OPTICAL TOMOGRAPHY

This is a continuation application under 35 USC 120 of PCT/EP2012/001639, filed Apr. 16, 2012, which claims priority to DE Application 10 2011 018 603.4 filed Apr. 21, 2011, and to U.S. Application 61/508,831, filed Jul. 18, 2011, the contents of each of which are incorporated by reference herein.

The invention relates to a method for detecting spatially structured sample volumes by means of coherent light and digital holography (DH). The invention also relates to a method for analyzing the depth structure of samples in accordance with optical coherence tomography (OCT).

Holography comprises the three-dimensional imaging of objects using coherent light, in particular laser light. Here the light is divided by a beam splitter into sample and reference arm, the sample beam illuminating the sample. Light that is reflected by the sample in different distances or backscattered is guided to a light-sensitive surface (e.g. the film in the camera) and superposed there with the reference light. By interference, a spatial light-intensity distribution, the hologram, is generated in the image plane.

In classical holography, a hologram is reconstructed optically, in that the developed hologram is again illuminated using a reference beam. The diffraction-wave field generated in the process exhibits a component that corresponds to the original object-wave field. Further components represent a conjugate image and the reference wave whose fraction is proportional to the original intensity of reference and object wave.

In digital holography, the light-sensitive surface is formed by an electronic light sensor (e.g. CCD or CMOS camera). A digitally stored hologram can be fed without a detour to an optical reconstruction of the further evaluation in a computation unit. For example, knowing the light-wave field of the reference beam, the light-wave field of the light returning from the sample can be calculated in any planes parallel to the camera plane. If the light-wave field in the camera plane is known, it can be made to propagate numerically, for example by applying the "angular spectrum" method, the Fresnel Transformation or another integral transformation.

The "angular spectrum" approach or the "parallel wave expansion" approach used in many cases for calculating the wave field in a reconstruction plane is based on a development of the object-wave field in the hologram plane $f(x, y, z=0)$ into plane waves $\exp(i(k_x x + k_y y))$, i.e., the 2D Fourier transform of the wave field is calculated. The transverse components of the wave numbers of the individual plane waves of the wave fields are thus known, that is to say the function $\tilde{f}(k_x, k_y, z=0)$. The term "transverse" shall always refer below to directions in the hologram plane. The direction at right angles to the hologram plane is annotated by the adjective "axial". In terms of apparatus, the hologram plane again coincides with the plane in which a measurement of light intensities takes place (→camera plane, see below).

The propagation of the fields now corresponds to the matching of the phases of these components as they have to be at a predetermined distance from the original plane. This is achieved by multiplication of each individual component $\tilde{f}(k_x, k_y, z=0)$ by the phase factor $\exp(ik_z z_0)$, $k_z$ designating the axial component of the wave number vector and being different for all components ($k_x, k_y$) in general. $z_0$ means the axial propagation distance. The component (in vacuum) is given as $$k_z(k, k_x, k_y) = \sqrt{k^2 - k_x^2 - k_y^2}, \quad (1)$$

$k=2\pi/\lambda$ representing the total wave number. Expressed mathematically, the propagated plane-wave decomposition is consequently calculated from the original one (in general the decomposition of the measured wave field) using $$\tilde{f}(k_x, k_y, z=z_0) = \exp(iz_0\sqrt{k^2 - k_x^2 - k_y^2})\tilde{f}(k_x, k_y, z=0). \quad (2)$$

In this way it is possible to calculate the wave-field distribution of the scattered light in arbitrary planes outside and inside the sample. In particular after recording the electronic hologram, reconstruction of the light-wave field in any selectable "reconstruction plane" can take place.

In volumes having consecutive partly-transparent structures (e.g. biological tissue), the wave field is composed of components that were reflected at different distances from the camera plane or were scattered by scatterers in different depth planes (parallel to the hologram plane). When a real image of the volume is reconstructed, the wave field appears in focus, while all other depth planes of the volume contribute an out-of-focus component to the reconstructed image.

Digital holography is very well suited for the fast detection of the surface of a sample if it lies in more than only one defined focus plane (for example because the surface is bent). If however the sample exhibits scattering structures in different depths, that lie one behind the other axially, also the wave-field components of such scatterers interfere with each other and adulterate the image.

It has already been recognized that tomographic data can be reconstructed using digital holography, if several wavelengths (e.g. tunable laser) are used and one hologram each is recorded for a—preferably equidistantly selected—sequence of wave numbers. The recorded holograms are all reconstructed for the same reconstruction plane, and the complex wave field generated in the process is superposed. During this numerical superposition of the waves having different wavelengths, only those components interfere that result from the focus plane, all other components are suppressed. The method is then repeated for further planes, so as to gain a depth image of the sample in the synopsis of all planes. Such a procedure is very complex numerically and can be practiced only with difficulty for the tomography of relatively large volumes. (Wavelength-Scanning Digital Interference Holography: L. Yu, M. K. Kim, Variable tomographic scanning with wavelength scanning digital interference holography, Optics Communications 260 (2006) 462-468 and M. K. Kim, Principles and techniques of digital holographic Microscopy, SPIE Reviews 018005-1 Vol. 1, 2010).

In the paper by Blazkiewicz et al., Experimental Demonstration of Signal-to-Noise-Ratio Improvement of Fourier-Domain Optical Coherence Tomography (I. P. Blazkiewicz, M. Gourlay, J. R. Tucker, A. D. Rakic, and A. V. Zvyagin, "Signal-to-noise ratio study of full-field Fourier-domain optical coherence tomography," Appl. Opt. 44, 7722-7729 (2005)) it is proposed to combine an FD OCT system (Fourier-Domain) with Fourier holography, the depth information being detected in parallel on all camera pixels for all measurement points of the sample. The aim of the paper is to avoid scanning the sample using the OCT measurement beam. In the process, the sample is illuminated in a two-dimensional manner, and the scattered light is imaged to infinity using a lens and brought onto the camera, i.e. the camera is arranged in the diffraction far field of the object structures. For several wavelengths of a tunable laser-light source, a Fourier hologram is generated, and the entirety of all holograms practically represents the 3D-Fourier transform of the sample structure. However, the optical design is only able to image the depth environment of a selected focus plane in the sample into the far field, and this results also only for this plane in an in-focus reconstruction. This system is therefore not able to reconstruct all planes of the sample in focus, without a reorientation of the measurement equipment being necessary for this. When the transverse resolution is increased, the sample range that can be imaged in focus becomes smaller drastically, since there is a fundamental connection between depths of focus and transverse resolution for imaging systems. This increases the number of necessary measurements with a shifted focal position even as a square function with the desired transverse resolution.

The patent specification U.S. Pat. No. 7,602,501 B2 deals at length with the evaluation of wavelength-dependent two-dimensional interferograms for calculating the three-dimensional scattering power of a sample, it being possible to dispense with moving parts in the measuring set-up (e.g. for phase modulation or refocusing). The specification teaches to formulate the measurement data as a result of a model of light scattering in the sample and then to invert this model so as to obtain a three-dimensional scattering model of the sample. Inverting an a priori not unambiguous invertible integral core represents an "ill-posed problem" that can be solved in general only using regularization measures. U.S. Pat. No. 7,602,501 B2, too, uses a focus plane in the sample that is imaged onto an electronic camera, as is common in OCT. By evaluation, it achieves a higher resolution of the scattering structures even significantly outside this focal plane, so that shifting the focal plane for scanning the entire sample volume is no longer necessary.

In U.S. Pat. No. 7,602,501 B2 it is not recognized that it may be more favorable to completely dispense with an imaging optics. This waiving in particular permits the application of methods of digital holography, using which it becomes avoidable to carry out the calculation of the sample scattering power as an inverting of a scattering model. Moreover, a—numerically simulated—measurement of the scattering power can then be carried out at any sample depths.

The conference contribution of Shabanov et al., "Broadband 3-D Digital Holography for Depth Structure Visualization" to the conference Digital Holography and Three-Dimensional Imaging (DH), Miami, USA, April 2010, present a method for 3D visualization of the depth structure of scattering biological samples having a high spatial resolution (10-15 µm) without scanning in the longitudinal or transverse direction. This method is based on holographically, digitally recording light waves scattered at the object for a discrete amount of spectral components and a digital reconstruction of the 3D image a posteriori.

The measurement apparatus of Shabanov et al., in addition to a digital camera and a tunable laser-light source, also uses a phase modulator for varying the reference-arm length. For a number of N used laser-light wavelengths, in each case only three images are recorded with different reference-light phases, i.e. 3*N images for subsequent evaluation are detected and stored.

The object of the invention is to propose a method for 3D-imaging of scattering samples, where a uniformly high three-dimensional resolution is achieved even across a large depth area of the sample with at the same time minimal loading of this sample by the radiation.

The aim of the invention is to determine the three-dimensional scattering power $S(x,y,z)$ of the sample. If it is known numerically—in an acceptable resolution, i.e. density of supporting points—, then any representation of three-dimensional data arrays for imaging can be employed using methods known per se, for example the calculation of any two-dimensional sections. It is described below how $S(x,y,z)$ can be determined for the entire sample what is meant here is the sample area for which the light backscattered from the sample can at all reach the detector using only one measurement and using only one numerical evaluation step.

The invention combines digital holography with FD-OCT (Fourier Domain OCT) in a novel way. At first, wavelength-dependent holograms of the sample are recorded using an electronic camera. The reference light is used in a manner known per se for calculating, in the camera plane, the electrical wave fields of the light scattered in the sample and to reconstruct them in an axially shifted reconstruction plane. This reconstruction plane can be situated in particular inside the sample. The inventive idea consists in superposing, in the computer, the reconstructed wave field in the reconstruction plane again using a reference light beam to obtain a two-dimensional numerical interferogram that can be evaluated like the OCT. The OCT evaluation pixel-by-pixel of the interferogram provides depth information from a layer of the sample in the surroundings of the reconstruction plane. In a way, shifting the OCT camera in any plane, in particular into the sample interior, is simulated numerically.

Since the reconstruction plane can be selected freely, any sample depth can be analyzed using the invention, and a three-dimensional image of the entire sample volume results. The requisite measurement data are recorded during a measurement prior to the numerical analysis and represent only a minimum stress of the sample by light.

A particular advantage of the invention is that the numerical evaluation actually does not have to take place layer for layer, but rather the calculation of the three-dimensional scattering power $S(x,y,z)$ can effectively take place in one computational step that comprises a Fourier transform of non-equidistant supporting points.

The invention is explained below in more detail:

The sample is illuminated using a tunable laser light source. The largest possible fraction of the light backscattered from the sample is to be detected using an electronic camera, a 2D light detector array. For this reason, the camera is arranged as closely as possible to the sample so that the curvature of the light-wave fronts can no longer be neglected. According to the invention, it is therefore the "Fresnel diffraction pattern" or also the "diffraction near field" of the sample that is recorded. The camera shall be able to detect light in the process that leaves at most at an angle of $\alpha_{max}$ relative to the optical axis. $\alpha_{max}$ determines the numerical aperture $NA = n \cdot \sin \alpha_{max}$ of the arrangement, n being the index of refraction of the medium.

By beam splitting, a reference light beam is collected from the laser light source and guided to the camera plane. Illumining using reference light is in general carried out such that a predetermined number of camera pixels is illuminated as uniformly as possible by reference light.

It is pointed out that the camera plane can likewise be replaced by a plane in which an optical image of the 2D light detector array is present. The imaging optics then guides the light that arrives in the plane of the image, further to the physical detector. For simplicity reasons, the camera plane will be referred to below in the sense that per definition a physical measurement of light intensities takes place there irrespective whether the 2D light detector array or only its image is situated in just this camera plane.

In the case of inventive methods, the sample is illuminated two-dimensionally. The light backscattered from the sample is guided directly onto the camera plane. No focus of the sample light beam exists in the sample as this is usually the case with confocal OCT. In particular, no plane of the sample is imaged by the sample light in focus onto the camera plane.

For the detection of holograms in the camera plane, the angle between sample and reference light beams is important. The angle between the local tangents on the reference and sample wave fronts determines the local spatial modulation frequency of the hologram. If the reference and sample lights of the wavelength λ impinge on the sensor at an angle θ, the local spatial frequency is given by $$f \approx \frac{2}{\lambda}\sin\frac{\theta}{2}.$$

It must be possible for the camera to scan this modulation frequency without artifacts. Therefore, the resolving power and the pixel number of digital cameras limit the maximum angle between sample and reference beams and thus also the image field and the usable NA.

To guarantee the smallest possible angles between reference and sample wave fronts on as many pixels of the 2D light detector array as possible, it may be appropriate to arrange a beam-dilating element, for example a spherical mirror, in the reference arm. The reference arm is preferably dilated spherically so that spherical wave fronts impinge on the detector. In this sense, the reference beam is thus divergent and exhibits a—virtual—focus in the area of the sample, i.e. at a distance from the camera plane that approximately corresponds to the distance of the sample from the camera plane. This virtual focus of the reference beam is to be referred to as reference focus.

The smallest local angle—i.e. the smallest modulation frequencies in the hologram—would be produced if the reference focus were centrally in the measurement volume. However, this would be unfavorable for reconstructing the light-wave fields since then a Fourier hologram would be obtained and no in-focus imaging of all planes of a volume would be achieved if the volume is significantly deeper than the Rayleigh length $l_R = \lambda/\pi NA^2$.

In general, during practical measurements, Fourier holograms can also not be completely rid of their constant background (DC component). If the DC component remains after converting the measured holograms into electrical field strengths, then this component is proportional to the reference wave after multiplication by the (conjugate) reference wave—a punctiform source that has its origin in the measurement volume. If the field is propagated into the measurement volume to the place of the reference focus, it is above all this punctiform source that is reconstructed, which than leaves to a dominant bright spot in the data that masks the reconstructed volume.

Therefore it is preferably the reference focus that is determined such that it is situated as closely as possible to the measurement volume, but outside the measurement volume. In the case of a known distance of the sample volume to be imaged from the camera plane, the element that dilates the reference beam is to be set up in an appropriate manner, for example by specifying the distance and/or the radius of curvature of the spherical mirror.

During tuning the laser light source, which preferably takes place monotonically between two interval boundaries of the wavelengths in a rising or falling manner, the camera records a plurality of holograms. N holograms are recorded for known wavelengths. Here N>100 and at least twice as large as the number of depth supporting points in the sample for which it is desired to determine scattering powers. Particularly preferably, N is even larger than 1000. Using laser sources and high-speed cameras that are available at present, in the presently existing measurement set-up the complete measurement of a sample can take place in 2.1 seconds at a resolution of 1024×1021 pixels and at a frame rate of 500 fps.

A shorter measurement time, preferably less than one second, particularly preferably less than 200 ms, is favorable if a proper motion of the sample (e.g. living tissue) is to be assumed since Doppler shifts of the laser light make the method particularly susceptible to failure in terms of movements. This is the case with medical applications, for example when examining the eye. If the requirements in terms of resolution and/or sample volume are restricted, such measurement times can already be achieved at present.

In principle, each photon backscattered from the sample in the angular range of the NA lands on the three-dimensional camera and can be evaluated in terms of its propagation direction and propagation length in the sample. In this way, the precise origin of the scattering can be determined for ballistic (simply scattered) photons.

In analogy to digital holography, when the reference wave that is in each case present is known, the detected holograms are converted for each wavelengths $\lambda_n$ complex light-wave fields $E_n(x, y, k_n = 2\pi/\lambda_n)$, n=1, . . . , N, x and y as pixel coordinates of the camera, it being possible for additional terms that originate from the DC component and the conjugate wave to be neglected at first. Specifically, the light intensity detected in the camera plane and registered on the pixels—the hologram—is divided by the pre-known reference wave. The wave field thus determined of the scattered sample light can then be propagated numerically axially in a manner known per se (here using the angular spectrum method as explained in the prior art, see above).

The basic idea of the invention is now to evaluate the propagation-time distribution of the propagated wave fields in the reconstruction plane in terms of the reference light for all $k_n$ so as to obtain additional depth information on the surroundings of the reconstruction plan. This can be viewed as a type of simulated OCT measurement in the reconstruction plane—perhaps inside the sample—, however, no physical superposition or intensity detection taking place here any longer. Rather all further steps are carried out only in the computer.

In principle, the propagation times already exist in the calculated phase data, but are however so to say "blurred" by the computational steps previously carried out. However, their reconstruction succeeds without problems by matching the phases of all spatial-frequency spectra $E_n(k_x,k_y,k_n)$ of the propagated light-wave fields. Below, the two-dimensional Fourier transforms of the light-wave fields along the axes that span the reconstruction plane of the camera plane are referred to below as transverse spatial-frequency spectra.

During the original measurement of the holograms, the phase differences correctly represent the propagation-time differences between reference and sample lights. If the electrical wavelength in the camera plane is now calculated using the measurement intensities by multiplication by the conjugate reference wave, the phase differences obtained reflect the propagation-time differences between sample and camera provided the reference-wave field is calculated using the correct phase, i.e. in particular using a phase in the reference plane that is constant over all wave numbers. To ensure a phase-neutral multiplication by the reference wave, multiplication by an additional phase is necessary that compensates the propagation time that is introduced.

For a plane wave, for example a constant phase factor is therefore used instead of a plane wave having a propagation time that corresponds to the distance z covered, i.e., exp(ikz) is replaced by exp(iφ), φ representing any constant independent of k.

A further example is a spherical wave R(x,y;k) having any propagation time in the camera plane.

$$R(x,y;k) = \exp(ik\sqrt{R^2+x^2+y^2}) \quad (3)$$

It is compensated by inserting an additional phase factor so that R(x,y;k) for any coordinate pair (x,y) no longer depends on the wave number k, i.e. R(x,y;k) is for example replaced by R'(x,y;k)

$$R'(x,y;k) = \exp(ik\sqrt{R^2+x^2+y^2} - ikR) \quad (4)$$

R' is then independent from the wave number k for the coordinate pair (x,y)=(0,0).

During propagation of a wave, a similar compensation has to be carried out. The propagation of the transverse space-frequency spectrum $f(k_x,k_y,z=0;k)$ into another plane is achieved by means of $$f(k_x,k_y,z;k) = \exp(iz\sqrt{k^2-k_x^2-k_y^2}) f(k_x,k_y,0;k) \quad (5)$$

So that no additional propagation-time shift is introduced during this step, the propagation core likewise has to be independent from the wave number k for any fixed transverse spatial frequency $(k_x,k_y)$. The propagator is then for example matched in this way:

$$f(k_x,k_y,z;k) = \exp(iz\sqrt{k^2-k_x^2-k_y^2} - izk) f(k_x,k_y,0;k), \quad (6)$$

In the case of this preferred choice of the phase matching, the components of the transverse spatial-frequency spectra for $(k_x,k_y)=(0,0)$ than experience no phase shift that is dependent on k.

As a general rule, each transverse space-frequency spectrum of the light-wave fields is multiplied, after propagation into the reconstruction plane, by a phase factor that is dependent on $k_n$, so that the components $E_n(k_{x0},k_{y0},k_n)$ of all N space-frequency spectra in the reconstruction plane assume the same value for a predetermined transverse space frequency $(k_{x0}, k_{y0})$. The choice of $k_{x0}$ and $k_{y0}$ is per se arbitrary, but preferably $k_{x0}=k_{y0}=0$ will be selected since the requisite phase factor then exhibits the most simple form.

After this, from the measured holograms a three-dimensional scattering-power distribution can be calculated in the surroundings of the reconstruction plane according to the formula $$S(x,y,z) = \mathcal{F}_{2k \to z}^{-1} [\mathcal{F}_{2D}^{-1} e^{-ikz_0} e^{ik2(k_x,k_y)z_0} \mathcal{F}_{2D}[E(x,y;k)]], \quad (7)$$

E(x, y, k) designating the calculated wave field in the camera plane, $z_0$ the desired reconstruction plane, $\mathcal{F}_{2D}$ the two-dimensional Fourier transform along x and y and $\mathcal{F}$ the one-dimensional Fourier transform from k to z.

The volume reconstructed according to (7) is, however, imaged in focus only in the depth surroundings around $z=z_0$ in the transverse direction. The scattering power of the sample is thus determined precisely at first only for a relatively slim layer of the sample at $z_0$, so that it can be called an imaging of the sample. The thickness of said layer is given in approximation by the Rayleigh length, i.e. by the numerical aperture (NA) of the measurement set-up. However when the NA increases, the Rayleigh length decreases. On the other hand, analogous to digital holography, the following is valid: the greater the NA, the higher the transverse resolution.

In contrast thereto, the axial resolution—inside the limits of the layer thickness by the Rayleigh length—is determined by the band width of the light source as with FD-OCTD and insofar independent of the NA. Here it is in particular possible to arrange the axial and transverse resolution by specifying the band width of the tunable laser and the specification of the numerical aperture in terms of equipment independent of each other. It is particularly favorable to arrange both resolutions to be approximately of the same size, as can be expected for 3D imaging.

According to what has been said above, the advantage of the invention can be seen in the fact that the weakness of digital holography when dealing with consecutive scattering structures is compensated by a one-dimensional spectral evaluation of simulated interferograms and thus overcome. Since the interferograms are only simulated and the reconstruction plane can be selected freely, the simulation can be repeated in any other sample depths. In terms of OCT, the limitation of the Rayleigh lengths is thus eliminated.

In this is to be seen the essential achievement of the inventive method: a single optical measurement where a plurality of two-dimensional holograms are recorded for a wavelength interval, is at the same time an FD-OCT measurement, carried out in parallel at a predetermined NA at all measurement locations in a predetermined sample surface area, across a measurement depth range in the sample that corresponds to a multiple of the Rayleigh length.

The applicability of the OCT interpretation of the measurement data across many Rayleigh lengths results from the propagatability of the wave fields that can be reconstructed from the spectra that are recorded in two-dimensions in parallel. Here the reference light fulfills two functions at the same time: it serves for the holographic reconstruction of the wave fields and the propagation-time measurement of the light in the manner of the OCT. So that the propagation times in the phases of the light-wave fields, calculated from the holograms and propagated thereafter, can be used for evaluating the depth information in the surroundings of the reconstruction plane, phase matching of the transverse space-frequency spectra is requisite that compensates the propagation-time differences between the propagated wave field and the reference light.

Basically, the measurement depth is only limited physically, precisely when no more light that can be evaluated sufficiently reaches the detector from the sample. To this extent, the invention enables the optimum OCT system that, using a—relatively fast—measurement, simultaneously detects all depths that can be achieved by means of the OCT measurement of a predetermined sample volume and supplies it to a 3D imaging by numerical evaluation. To re-adjust the measurement set-up and any further measurements are no longer necessary.

So this can be exploited in full, in the discussion further above of a layer the arbitrarily selected coordinate $z=z_0$ has to be replaced by another choice. For example it is possible that the data set $E_n(x, y, k_n=2\pi/\lambda_n)$, n=1, . . . , N is not propagated to $z_0$, but to $z_0$, but to $z_0+\Delta z$ without requiring any further additional measurement. The value $$\Delta z = \frac{\lambda_0}{\pi NA^2} \quad (8)$$

$\lambda_0$ as center wavelength of the predetermined wavelength interval of the tunable laser light source is a suitable choice since the pre-calculated scattering power distribution in the surroundings of $z=z_0+\Delta z$ was out of focus and unsuitable for 3D imaging. Again the propagation of the wave fields and the one-dimensional Fourier transform take place along k, and the image of a layer is again obtained in an analogous manner, this time however at a different depth of the sample. This procedure "layer-by-layer" can be continued until all measurable layers of the sample are analyzed and the results have been merged to a volume data set.

After it has been explained how the scattering power $S$ (x, y, z) can be determined for the entire sample using a resolution that can be selected in the axial and transverse directions by specifying the set-up, this object of the invention is in principle solved.

However, according to what has been said so far, in particular the transverse resolution is not of the same quality at all depths if the thicknesses $\Delta z$ of the calculated layers are selected too large. The best transverse resolution is always obtained directly in the reconstruction plane while above and below it, fuzziness due to diverging light beams occurs.

However, this is no deficit of the measurement method, but an artifact of the numeric evaluation. If the scattering power would be calculated for infinitesimally thin layers, i.e. if the layer thicknesses $\Delta z$ are allowed to assume any arbitrary smallness ($\Delta z \rightarrow 0$), the scattering power $S$ (x, y, z) for each depth z would in each case result via the formula $$S(x,y,z) = \mathcal{F}_{2k \rightarrow z'}^{-1}[\mathcal{F}_{2D}^{-1} e^{-ik(z+z_{ref})} e^{ik_z(k,k_x,k_y)(z+z_{ref})}$$
$$\mathcal{F}_{2D}[E(x,y;k)]]|_{z'=z} \quad (9)$$

The reconstruction distance $z_0$ from (7) is here split into a distance $z_{ref}$ from a first reconstruction plane and a distance between this first reconstruction plane and a second one inside the sample at the coordinate z, i.e. $z_0 = z + z_{ref}$. (Explanation see below).

The numerical evaluation of the formula (9) for each fixed choice of the coordinate z would unfortunately amount to an enormous computational effort. It would be comparable to the work of Kim et al. where a purely holographic reconstruction takes place. The advantage of the OCT evaluation included herein would be lost.

However, it is particularly advantageous that in (9) the sequence of the two Fourier transformations to be carried out last can be swapped and thus the one-dimensional numerical integration over the axial direction can be carried out first. (9) then becomes:

$$S(x, y, z) = \mathcal{F}_{2D}^{-1}[\mathcal{F}_{2k \rightarrow z}^{-1}[e^{-ik(z'+z_{ref})} e^{+ik_z(k,k_x,k_y)(z'+z_{ref})} \mathcal{F}_{2D}[E(x, y; k)]]]$$
$$= \mathcal{F}_{2D}^{-1}\left[\int_{\mathbb{R}} d(2k) e^{i2kz} e^{-ik(z+z_{ref})} e^{ik_z(z+z_{ref})} \mathcal{F}_{2D}[E(x, y; k)]\right]$$
$$= 2\mathcal{F}_{2D}^{-1}\left[\int_{\mathbb{R}} dk e^{i(k_z+k)z}\left(e^{i(k_z-k)z_{ref}} \mathcal{F}_{2D}[E(x, y; k)]\right)\right].$$

Swapping the Fourier transformations implies an interruption in the propagation in the first reconstruction plane. The further propagation is, however, also carried out, but it now takes place simultaneously in the course of the one-dimensional Fourier transformation along the optical axis of the sample light with the calculation of the depth-dependent scattering powers of the entire sample depth. Even though this makes the numerical implementation of the one-dimensional Fourier transformation a bit more complex, the result that can be calculated in this way presents a so-called "complete reconstruction" of the sample for all measurement depths at a uniform resolution without a reconstruction layer-for-layer still being necessary. For the complete reconstruction, preferably the first reconstruction plane is selected at a specific distance from the camera plane.

For each OCT image a measurement window exists, i.e. an axial area in z (a few millimeters) that can be represented. This area is a function of the width of the wavelength interval and of the sample rate of the OCT camera. For N detected wavelengths, N/2+1 depth supporting points can be discriminate. The associated depth interval is in general limited by at least Nyquist plane. The Nyquist plane exhibits the maximum propagation-time difference of the scattered light relative to the reference light that can still be detected in terms of the metrological sampling and is thus a plane in the sample from which scattering events can just about be unambiguously associated with a depth. The second limitation of the depth interval is usually the reference plane from which scattered light returned to the 2D light detector array does not exhibit any difference in the propagation time relative to the reference light.

For the implementation of the integration according to equation (10) it is very advantageous to set the first reconstruction plane as the null plane of the z axis and to know in the process that all scattering structures of the sample are on the same side of the z axis. Therefore it is recommended to select the previously mentioned reference plane whose position relative to the sample can best be controlled in terms of apparatus, as the first reconstruction plane. Particularly preferably, the reference plane is situated slightly outside the sample, for example by setting the instrumental reference-arm length in such a way as it is also common in FD-OCT. In principle, it would also be possible to select the Nyquist plane as the first reconstruction plane, but its position is difficult to define.

For calculating the scattering power $S$ (x, y, z) the integral transformation $\int_{\mathbb{R}} dk e^{i(k_s+k)z} f(k)$ for a function $f(k)$ has to be carried out. The numerical calculation of the integral for the data set $f(k_n)$, $n=0, \ldots, N \ldots 1$ can be expressed as $$\sum_{n=0}^{N-1} e^{i\frac{2\pi}{N}(k_z(k_n,k_x,k_y)+k_n)z_m} f(k_n). \quad (11)$$

The explicit calculation of a Fourier sum can be carried out by means of a Fast-Fourier-Transform (FFT), but efficient algorithms for this purpose need an equidistant set of k supporting points. In (11) however this is precisely not the case. Therefore one substitutes $\kappa_n = k_n + k_z$ with $k_z^2 = k_n^2 - k_x^2 - k_y^2$, $k_z$ itself being a function of $k_n$ and also of the pixel coordinates (x,y). If $k_n$ is written as a function of the independent variable $\kappa_n$, then $$k_n = (\kappa_n^2 + k_x^2 + k_y^2)/(2\kappa_n), \quad (12)$$

is found and this sum (11) can be then calculated fast if the function $f(k_n(\kappa_n))$ is interpolated onto a set of non-equidistant supporting points $k'_n$ with the attribute (12) for an equidistant set of $\kappa_n$. The integration task is practically converted into an interpolation task. A suitable interpolation can be carried out in different ways that are known to the person skilled in the art, for example linear interpolation, spline interpolation, Fourier interpolation, Sinc interpolation.

By discretization, the integration task of equation (10) becomes a summing task according to (11) which again requires a Fourier transformation onto non-equidistant supporting points. An algorithm that can carry out a non-equidistant Fourier transformation is to be called NFFT in short. One possibility of NFFT exists, as outlined, in an FFT subsequent to an interpolation of the function, to be transformed, onto to the non-equidistant supporting points. Other NFFT algorithms that could possibly dispensed with data interpolation may also be suitable.

The NFFT enables a numerical calculation of scattering powers onto principally equidistant depth supporting points that are also to be called reconstruction depths. In some cases it may happen that the distance between two reconstruction depths $z_m$ and $z_{m+1}$ changes by a known factor. This can happen e.g. when using numerical magnifications that change the axial reconstruction distance or when reconstructing the scattering in media having an index n of refraction. In this case, as a remedy the $\kappa_n$ axes (to clarify: each pixel (x,y) exhibits its own $\kappa_n$ axis) can be scaled with the inverse value of said factor so as to compensate numerically the spatial change in length. In practice, for example the interpolations have to be carried out on a scaled supporting-point set.

If the index of refraction of the sample even varies across the measurement depth, then also the distances of the reconstruction depths vary across the measurement depth. This can only be compensated by means of a Fourier transformation having non-equidistant supporting points in the wave number and also in the depth range (in short: NNFFT) so that an in-focus imaging in all measurement depths can continue to be guaranteed.

The inventive evaluation can be summarized as follows:
1. The recorded data set (camera images) $I_n(x, y, k_n)$ is calculated back into complex wave fields $E_n(x, y, k_n)$ as a result of the known reference wave. Other terms (noise, the DC component, the conjugate field) are eliminated or neglected.
2. The two-dimensional Fourier transformation (i.e. the plane-wave-decomposition or the angular spectrum) $\tilde{E}(k_x, k_y, k_n)$ of the individual wave fields $E_n(x, y, k_n)$ is carried out.
3. The data sets thus generated are propagated to the reference plane by multiplying all data points $\tilde{E}(k_x, k_y, k_n)$ with $e^{i(k_z(k_n, k_x, k_y) - k_n)z_{ref}}$. This step comprises in addition to the propagation also the phase correction by the factor exp $(-ik_n z_{ref})$ to maintain the propagation-time differences between sample and reference light.
4. Using the data $\tilde{E}(k_x, k_y, k_n)$ thus obtained, an NFFT with the supporting points established by $k_z(k_n, k_x, k_y) + k_n$ is carried out. The angular spectrum for all depths is obtained, i.e. $\tilde{E}(k_x, k_y, z_m)$.
5. The data $\tilde{E}(k_x, k_y, z_m)$ thus calculated are transformed back into the spatial domain (inverse two-dimensional Fourier transformation along the axes $k_x$ and $k_y$).

The problem, that is at first to be employed, of the contributions of multiple scattering events that are suppressed in OCT by confocal images has in practice proved to be not serious. Even though these multiple scattering events occur, they lead to a significant degradation of the structural data obtained only in the case of great measurement depths in the sample.

Using the means of the invention, it is readily possible to obtain—in a few seconds or even in fractions of a second—good three-dimensional structural information on a depth range of more than ten Rayleigh lengths by recording a single set of holograms in the predetermined wavelength interval.

Figure 1:
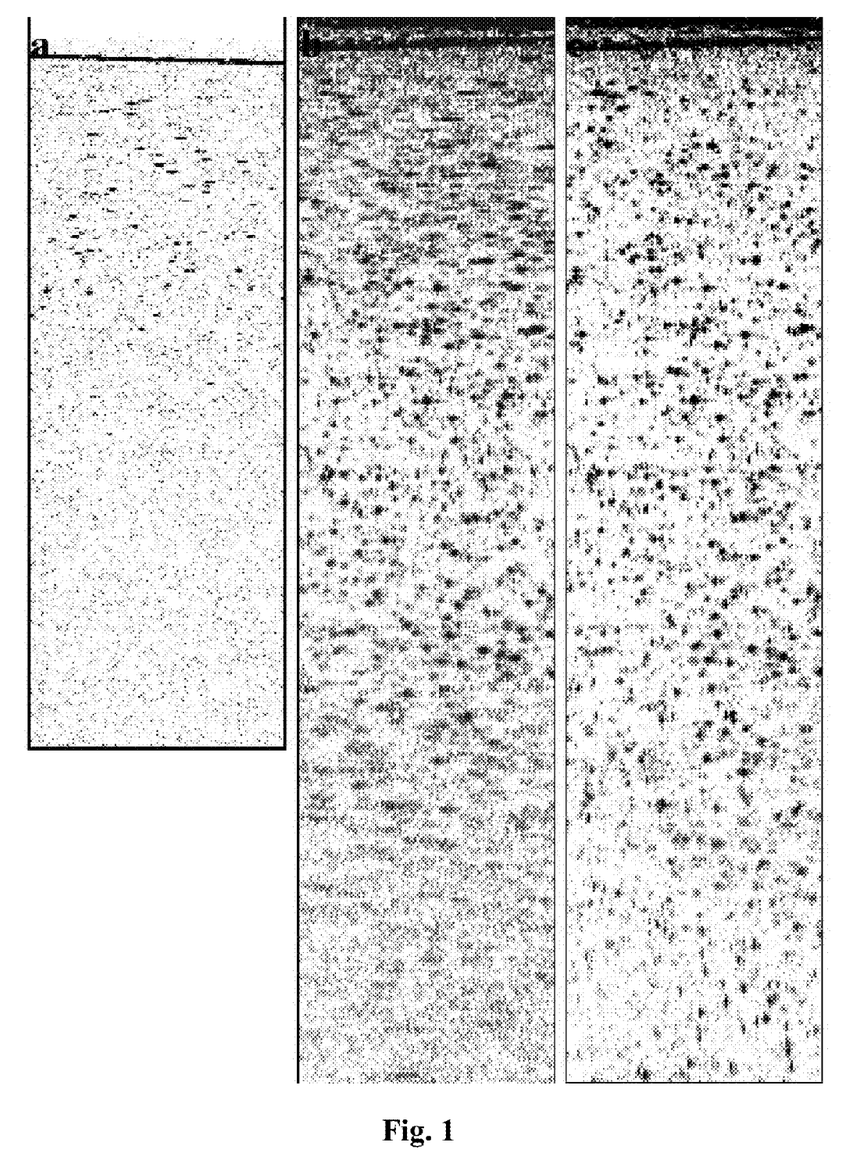

To illustrate this, figures of measurement results are now presented:

FIG. 1 shows tomograms, shown inverted, of a synthetic scattering sample (P. D. Wooliams, R. A. Ferguson, C. Hart, A. Grimwood, P. H. Tomlins, *App. Optics, Vol.* 49, *No.* 11, 2014-2021, 2010) consisting of a polyurethane resin into which spherical red iron-oxide nanoparticles were embedded that exhibit a diameter between 300-800 nm. FIG. 1 *a*) shows the result of a measurement of the scattering sample using a confocally scanning OCT having an NA of approximately 0.06. In the area of the confocal focus, the individual scatterers can be clearly seen. Outside, the resolution and also the intensity of the scatterer decrease. A measurement according to the inventive method using an NA of approximately 0.07 and a reconstruction of an individual sample layer can be seen in FIG. 1 *b*). In the reconstruction distance, the resolution of the scattering sample is diffraction-limited and decreases outside as can be expected. In contrast to FIG. 1 *a*), the intensity is not limited by confocal gating. The measurement in FIG. 1 *c*) is identical to the measurement of b), this time, however, the entire depth range is reconstructed via NFFT evaluation. It can be recognized that the resolution is diffraction-limited over several Rayleigh lengths. Neither the intensity, nor the resolution shows variations across the depth axis (running from top to bottom in all images) of the sample.

Figure 2:
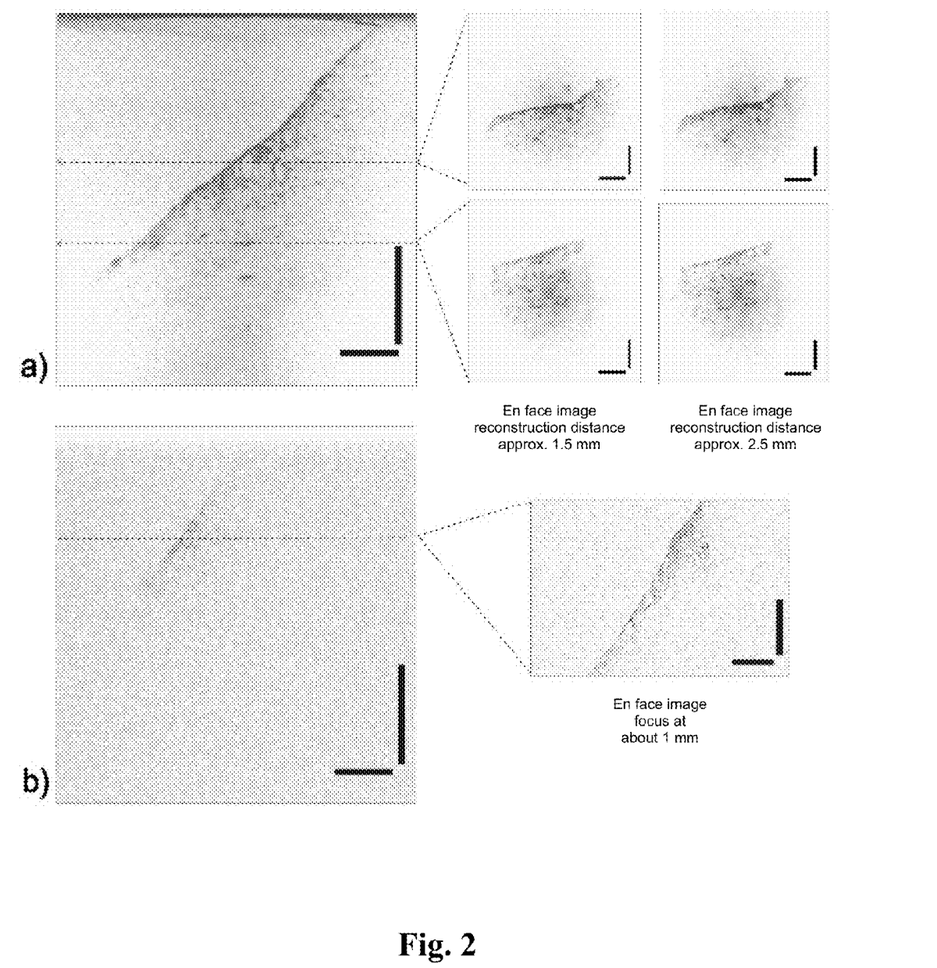

FIG. 2 shows tomograms, illustrated in an inverted manner, of a grape that is placed at an inclined angle. In each case an image of a measurement system of inventive design having an NA of 0.07 (a) was compared to a confocal OCT system having an NA of 0.06 (b). The reconstruction distance is varied, and en face images for two sections having a reconstruction distance of 1.5 mm or 2.5 mm are shown. The focus of the confocal OCT is specified at 1 mm depth. The loss of intensity outside the Rayleigh length for the confocal OCT can be clearly seen. In contrast thereto, the structures that scatter in the images of FIG. 2 *a*) can be clearly seen beyond the Rayleigh length. In the en face images, the effect as a result of different reconstruction distances can be observed. All scales used are 1 mm.

Figure 3:
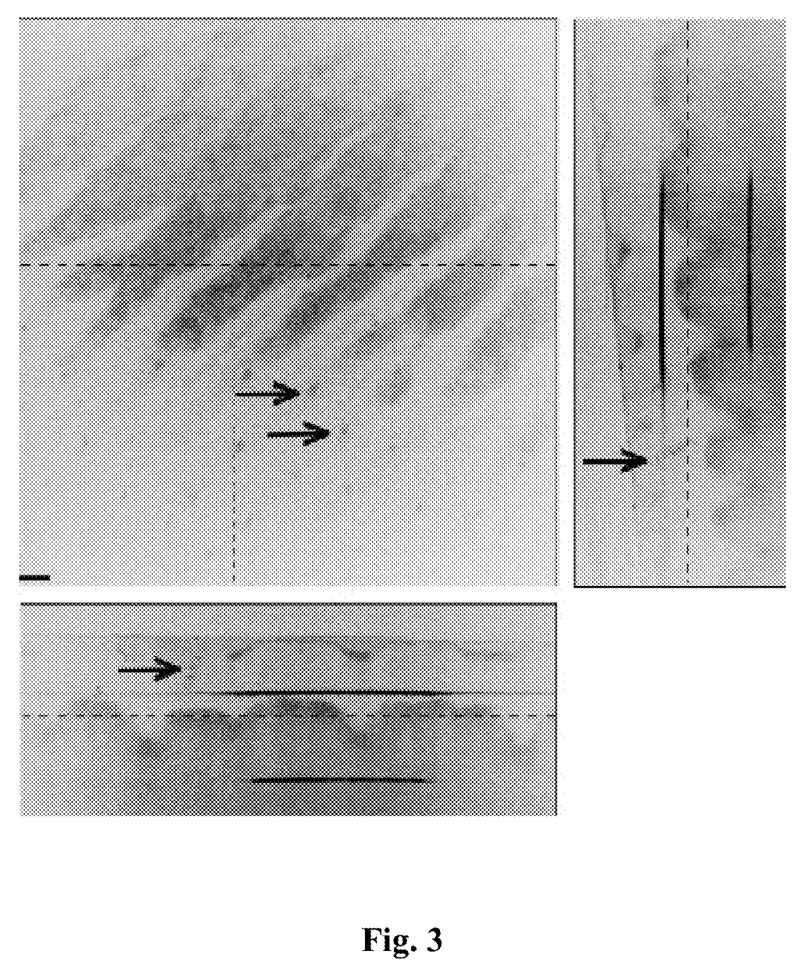

In FIG. 3, three perpendicular sections through the finger tip of a human, measured in vivo, are shown (inverted illustration). The measurement was carried out using the method described here for determining the entire scattering-power distribution within a few seconds. During the evaluation, a reconstruction plane was placed in the plane of the perspiratory glands. The horizontal lines in the image are artifacts that are produced by reflections from a glass plate in front of the sensor of the camera. The dashed lines show the respective position of the other sections.

In principle, the invention can be carried out using any device for digital holography and a tunable laser source. A high tuning speed of the light source and a very high imaging speed of the electronic camera are very recommendable, in particular for the in-vivo application.

To supplement this, the possibilities for compensating movement artifacts in numerical control shall also be mentioned.

For in-vivo images, the present speeds of digital cameras entail the problem that the object is frequently moving during the recording of the image, leading to artifacts in the tomograms. Here movements in the z-direction, i.e. along the optical axis, are most problematic since in addition to the actual physical movements, the reconstructed object is shifted on account of the Doppler effect. The z-movements also have the characteristic that they change the propagation time of the light for different wave numbers, leading to effects in images that cannot be discriminated from dispersion.

Movements can be determined by means of a time-frequency analysis of the signal measured over the wave number k since a movement varying in time characteristically alters, by means of Doppler shift, the signal for all uniformly moving volume parts. For this purpose, for example a "short-time" Fourier transformation (STFT) lends itself, using which global movements of the object can be understood: a specific wave number range that corresponds to a time interval that is shorter than the entire imaging time, is objected to window formation. In general, this will reduce the resolution after the reconstruction, however the object is now no longer characterized in such a strong manner by movement artifacts since the window formation has selected a shorter imaging time. If this is carried out for a plurality of central wave numbers and thus measurement instances, the movements can be detected and determined in the individually reconstructed tomograms. In principle, this information can be extracted using all transformations that permit a time-frequency representation of the signal (STFT, Wavelet transformation, Gabor transformation, etc.). To extract the movement from the time-frequency representation, for example a cross correlation of the short-term images can be carried out.

If the movement is known, the effect of the movement can be reversed again by multiplication by inverse phases belonging to the movements in the Fourier space of the tomograms. Here care has to be taken that a phase change by $\exp(i\phi(k))$ as a result of STFT causes a shifting of the individual images by $\partial_k \phi(k)$:

$$STFT_{k_0}[\tilde{f}(k) \cdot \exp(i\phi(k))] = \int_{k_0 - \Delta k}^{k_0 + \Delta k} dk \tilde{f}(k) \exp(i(kz + \phi(k)))$$

$$= \int_{k_0 - \Delta k}^{k_0 + \Delta k} dk \tilde{f}(k) \exp$$

$$[i(kz + \phi(k_0) + k\partial_k \phi(k)|_{k=k_0} + O(k^2))]$$

$$\approx \exp(i\phi(k_0)) \cdot \tilde{f}(z + \partial_k \phi(k)|_{k=k_0})$$

Consequently, the shift of the short acquisition-time images determined from the cross correlation has to be integrated in order to find a suitable phase compensation.

A different group velocity dispersion can occur in the sample and reference arms if an asymmetric set-up of sample and reference arms is selected, as e.g. in the case of a Mach-Zehnder interferometer. This leads to a reduction of resolution and signal strength. Mathematically, the differences in dispersion become obvious in an additional phase that is a function of the wave number or the wavelength, i.e. the spectrum $S(\lambda)$ is specified by $$S(\lambda) = 2Re\int dz \tilde{f}(z) \exp(ik(\lambda)z + i\phi(\lambda)) + \ldots,\quad (14)$$

$\phi(\lambda)$ being determined by the dispersion. The phase can be compensated by multiplying the data before the Fourier transformation along k or along $k_z$ by a suitable phase function that is dependent on the wavelength, i.e. using $\exp(-i\phi(\lambda))$. On account of the identical effect of dispersion and movement of the object in the axial direction during the measurement, this phase function can be determined with the same algorithm as in the case of the movement correction. Since as a rule the group velocity dispersion is constant, the determination of the phase function does not have to be repeated for each measurement.

The dispersion can be determined experimentally by using two mirrors at different depths. From this the correct phase multipliers can be determined using Hilbert transforms. If two mirrors at the depths $z_1$ and $z_2$ relative to the reference are given, the associated interference signals $S_1(\lambda)$ and $S_2(\lambda)$ are provided by $$S_1(\lambda) = 2Re\int_{-\infty}^{+\infty} dz \delta(z-z_1) \cdot \exp(ik(\lambda)z_1 + i\phi(\lambda)) = 2\cos(k(\lambda)z_1 + \phi(\lambda))$$

$$S_2(\lambda) = 2Re\int_{-\infty}^{+\infty} dz \delta(z-z_2) \cdot \exp(ik(\lambda)z_2 + i\phi(\lambda)) = 2\cos(k(\lambda)z_2 + \phi(\lambda)) \quad (15)$$

If additional terms are neglected (DC terms, auto-correlations, no further signals, etc.) and if $z_1 > 0$ and $z_2 > 0$, the Hilbert transformation of these signals is given by $$S_1 + i\mathcal{H}[S_1(\lambda)] = 2\exp(ik(\lambda)z_1 + i\phi(\lambda))$$

$$S_2 + i\mathcal{H}[S_2(\lambda)] = 2\exp(ik(\lambda)z_2 + i\phi(\lambda)) \quad (16)$$

If the mirror positions $z_1$ and $z_2$ are known, that can be obtained from the reconstructed data (comparable to an OCT A scan), the required phase $\phi(\lambda)$ and $k(\lambda)$ can be resolved to:

$$k(\lambda) = -\frac{1}{(z_1 - z_2)}[\arg(S_1(\lambda) + \mathcal{H}[S_1(\lambda)]) - \arg(S_2(\lambda) + \mathcal{H}[S_2(\lambda)])] \quad (17)$$

$$\phi(\lambda) = \frac{1}{(z_1 - z_2)}[z_2 \arg(S_1(\lambda) + \mathcal{H}[S_1(\lambda)]) - z_1 \arg(S_2(\lambda) + \mathcal{H}[S_2(\lambda)])]$$

Here, $\lambda$ does not necessarily have to represent the wavelength, but is the variable during which there was a linear sweeping with time, i.e. $\lambda(t) = \lambda_0 + \lambda_1 t$.

For this method however, only one mirror imaging using only one depth is required if either there is no dispersion, that is $\phi(\lambda(k)) = \phi_0 + \phi_1{}^k$ at constant $\phi_0$ and $\phi_1$ or if there was a linear sweeping in k, that is when $k(\lambda) = k_0 + k_1 \lambda$ with constant $k_0$ and $k_1$.

In summary it is to be emphasized that artifacts in the propagation-time differences between reference and sample light can occur due to group velocity dispersion or as a result of a translation (for example proper motion) of the sample, however, they can be compensated by a further phase multiplication of the transverse space-frequency spectra. Here it is important that the phase factors that are themselves a function of $k_n$, have to be introduced prior to the one-dimensional Fourier transformation for calculating the scattering powers.

We claim:

1. A method for 3D imaging of a scattering sample, in particular for determining the spatial scattering-power distribution—S(x,y,z) of the sample, comprising:
   a. splitting laser light having a wavelength that can be selected within a predetermined band width, into a sample and a reference light beam,
   b. illumining the sample at N different wavelengths $\lambda_n$, n=1, . . . , N, and returning the light scattered in the sample and also the reference light onto a 2D light detector array,
   c. superposing the scattered sample light with the reference light on the 2D light detector array and recording in each case one hologram for each of the N wavelengths,
   d. calculating the electric wave field scattered in the sample for each of the N wavelengths in the plane of the 2D light detector array,
   e. propagating all calculated wave fields in a predetermined reconstruction plane that is aligned perpendicular to the optical axis of the sample light beam,
   f. calculating the transverse space-frequency spectrum $E_n(k_x, k_y, k_n)$, with $k_n = 2\pi/\lambda_n$ of the electric wave field scattered in the sample and propagated in the reconstruction plane for each of the N wavelengths,
   g. phase matching of the transverse space-frequency spectrum for each of the N wavelengths for compensation of the propagation-time differences produced by d) or e) between the propagated wave field and the reference light,
   h. calculating the depth-dependent scattering-power spectrum $S(k_x, k_y, z)$ by one-dimensional Fourier transformation of the space-frequency spectra for each transverse space frequency $(k_x, k_y)$ along the optical axis of the sample beam, and
   i. calculating the scattering power S(x,y,z) in at least one layer of the sample in the surroundings of the reconstruction plane,
   wherein phase matching takes place by multiplying each transverse space-frequency spectrum by a phase factor as a function of $k_n$ so that the components $E_n(k_{x0},k_{y0},k_n)$ of all N space-frequency spectra in the reconstruction plane assume the same value for a predetermined transverse space frequency $(k_{x0}, k_{y0})$.

2. The method according to claim 1, wherein the reconstruction plane is predetermined inside the sample.

3. The method according to claim 2, wherein the calculation of the scattering power S(x,y,z) takes place for a plurality of reconstruction planes or layers of the sample spaced along the optical axis of the sample light beam and these results are combined in the computer to a scattering-power distribution for the entire sample.

4. The method according to claim 1, wherein the reconstruction plane is predetermined in such a manner that light scattered in the reconstruction plane and returned to the 2D light detector array exhibits no propagation-time difference to the reference beam.

5. The method according to claim 1, further comprising numeric compensation of artifacts by sample movement or group velocity dispersion by multiplication of all transverse space-frequency spectra by a phase factor in each case dependent on the respective $k_n$ prior to carrying out the one-dimensional Fourier transformation.

6. The method according to claim 4, wherein the one-dimensional Fourier transformation is carried out as a Fast Fourier Transform (FFT) across a non-equidistant supporting-point set that is dependent on the respective space frequency $(k_x, k_y)$, the space-frequency spectra being previously interpolated onto these supporting points.

7. The method according to claim 1, wherein a beam-spreading element is provided in the reference arm that spreads spherically the reference light before it impinges on the 2D light detector array.

8. The method according to claim 7, wherein the reference light exhibits a focus in the proximity of the sample area to be investigated outside the sample.

9. The method according to claim 1, wherein not fewer than N=100 different wavelengths are used.

* * * * *